United States Patent [19]
Axel et al.

[11] Patent Number: 5,149,636
[45] Date of Patent: Sep. 22, 1992

[54] METHOD FOR INTRODUCING CLONED, AMPLIFIABLE GENES INTO EUCARYOTIC CELLS AND FOR PRODUCING PROTEINACEOUS PRODUCTS

[75] Inventors: Richard Axel; James M. Roberts, both of New York, N.Y.

[73] Assignee: Trustees of Columbia University in the City of New York, New York, N.Y.

[21] Appl. No.: 249,454

[22] Filed: Sep. 26, 1988

Related U.S. Application Data

[63] Continuation of Ser. No. 103,807, Oct. 1, 1987, abandoned, which is a continuation of Ser. No. 683,251, Dec. 17, 1984, abandoned, which is a continuation of Ser. No. 358,206, Mar. 15, 1982, abandoned.

[51] Int. Cl.$^5$ .............. C12P 21/02; C12Q 1/68; C12N 15/10
[52] U.S. Cl. ................. 435/69.1; 435/69.2; 435/6; 435/172.3; 435/240.2; 435/240.4; 435/320.1; 435/811; 435/948; 435/69.3; 435/69.4; 435/69.51; 435/69.6; 435/91; 435/191; 435/193; 435/194; 435/255; 514/2; 514/3; 514/4; 514/23; 935/4; 935/27; 935/31; 935/42; 935/56; 935/58; 935/66
[58] Field of Search .................. 935/4, 27, 31, 42, 56, 935/58, 66; 435/68, 172.3, 70, 240.2, 241, 317, 811, 948, 6; 424/85; 514/2, 3, 4, 23

[56] References Cited

U.S. PATENT DOCUMENTS
4,399,216  8/1983  Axel ................. 435/172.3
4,634,665  1/1987  Axel ................. 435/172.3

FOREIGN PATENT DOCUMENTS
8102426  9/1981  PCT Int'l Appl. .
8102425  9/1981  World Int. Prop. O. .

Primary Examiner—Robert A. Wax
Assistant Examiner—F. Tsung
Attorney, Agent, or Firm—John P. White

[57] ABSTRACT

Multiple copies of a foreign DNA I coding for the production of a protein may be introduced into eucaryotic cells by cotransforming suitable cells with foreign DNA I and with foreign DNA II which includes a functionally deficient, amplifiable gene coding for a selectable or identifiable trait, preferably carried on the same DNA molecule as a foreign DNA III, which includes a functional, amplifiable gene coding for another selectable or identifiable trait. The cotransformation is carried out under suitable conditions permitting selection or identification of cells expressing the gene on DNA I or that on DNA III, but not that on DNA II. The cotransformed cells so identified or selected are recovered and cloned under conditions where the functionally deficient gene on DNA II is expressed. Cells expressing the gene on DNA II are recovered. They contain multiple copies of DNA I. This method can be used to produce mRNA transcripts or protein products such as human and animal growth hormone, insulin and the like.

50 Claims, 1 Drawing Sheet

Fig. 1.

METHOD FOR INTRODUCING CLONED, AMPLIFIABLE GENES INTO EUCARYOTIC CELLS AND FOR PRODUCING PROTEINACEOUS PRODUCTS

The invention disclosed herein was made with Government support under Grant No. 2 PO1 23767 from the Department of Health and Human Services. Accordingly, the U.S. Government has certain rights in this invention.

This application is a continuation of U.S. Ser. No. 103,807, filed Oct. 1, 1987 now abandoned, which is a continuation of U.S. Ser. No. 683,251, filed Dec. 17, 1984, now abandoned, which is a continuation of U.S. Ser. No. 358,206, filed Mar. 15, 1982, now abandoned.

FIELD OF THE INVENTION

This invention relates to the introduction and expression in eucaryotic cells of deoxyribonucleic acid molecules (DNA) which include genes coding for proteinaceous products. The invention may be used to modify the genetic make-up of cells derived from or associated with organisms classified under the SuperKingdom Eucaryotes, including organisms of the Plant and Animal Kingdoms. More particularly, the invention concerns improved methods of DNA-mediated gene transfer for introduction of cloned, amplifiable genes into eucaryotic cells and for production of products encoded thereby.

BACKGROUND OF THE INVENTION

The use of cotransformation to introduce foreign DNA into eucaryotic cells has been described. PCT International Publication Numbers WO81/02425 and WO81/02426, published Sept. 3, 1981, and scientific articles identified therein. Gene amplification as a means for obtaining enhanced gene expression has also been described. Alt, F. W., et al., (1978). J. Biol. Chem. 253, 1357–1370, and Wahl, G. M., et al., (1979). J. Biol. Chem. 254, 8678–8689. Eucaryotic gene promoters are known. McKnight, S. L. et al., (1981). Cell 25, 385–398. Finally, cloned amplifiable genes have been described. Lee, D. E., et al., (1981). Nature 294, 228–232.

Known, cloned amplifiable genes whose amplification can be selected for include those whose product either (a) directly or indirectly interacts with an inhibitor of cell growth so as to render the inhibitor ineffective, or (b) is necessary for cell survival and can be inhibited by exogenously supplied substances. In both instances, the nature of the amplification process is such that increasing amounts of gene product must be produced in the presence of increasing amounts of inhibitor in order for cells to survive.

Gene products of type (b) include dihydrofolate reductase (DHFR) and aspartate transcarbamoylase (ATCase), which are amplified in cells resistant to high concentrations of methotrexate and PALA, respectively. The ATCase gene has been cloned. However, it has not been transformed into animal cells and shown to amplify. The intact DHFR gene has not been cloned. Expressing cDNAs of DHFR have been constructed and cloned, but have not been shown to amplify. Gene products of type (a) include the cloned, bacterial neomycin resistance gene whose expression in eucaryotes has been demonstrated. However, amplification of this gene has not been demonstrated.

The present invention discloses an unexpected, alternative route to amplification. Specific mutations can be introduced into genes coding for selectable or identifiable biochemical markers so as to render the genes functionally deficient. Following transformation, rare variant cell subclones can be identified which greatly amplify the expression of the mutant gene so that expression occurs at levels characteristic of the normal gene.

Specifically, a system involving gene transfer has been developed to study the nature of genetic rearrangements which are responsible for activation of mutant genes in mammalian cells. Cotransformation has been used to introduce a single copy of a plasmid containing an intact adenine phosphoribosyltransferase (aprt) gene along with a truncated thymidine kinase (tk) gene lacking its promoter sequence, into aprt$^-$ tk$^-$ mouse cells. Cells containing this plasmid transform to the aprt$^+$ phenotype but remain tk$^-$. Rare variants which mutate to the tk$^+$ phenotype were considered likely to reveal some form of DNA rearrangement. All tk$^+$ variants analyzed result from dramatic amplification of the promoterless tk gene along with significant lengths of flanking sequences. No other source of rearrangements are observed in over 40 tk$^+$ mutants examined.

One striking feature of these amplified aprt$^+$ tk$^+$ clones is the rate at which aprt$^-$ tk$^+$ variants appear. Examination of the structure of the amplified DNA indicates that all amplified units within a given aprt$^-$ cell bear an identical mutation. These data suggest that a correction procession is occurring at high frequency which may be designed to maintain sequence homogeneity within repeated genetic elements.

SUMMARY OF THE INVENTION

Multiple copies of a foreign DNA I which includes a functional, amplifiable gene coding for production of a desired proteinaceous product may be introduced into eucaryotic cells. Suitable eucaryotic cells are cotransformed with foreign DNA I and a foreign DNA II which includes a functionally deficient, amplifiable gene coding for a selectable or identifiable trait. The cotransformation is carried out under suitable conditions permitting production of the protein product, but not expression of the trait encoded by DNA II. Cotransformed eucaryotic cells producing the desired product are recovered and cloned under appropriate conditions permitting expression of the trait encoded by DNA II. The cloned, cotransformed cells are selected or identified on the basis of expression of this trait and recovered. The recovered cells contain multiple copies of DNA I and can be used to produce messenger RNA transcript or proteinaceous product.

In a preferred embodiment of the invention, multiple copies of foreign DNA I are introduced into suitable eucaryotic cells by cotransforming the cells with DNA I and with a deoxyribonucleic acid molecule comprising a foreign DNA II which includes a functionally deficient, amplifiable gene coding for a selectable or identifiable trait and a foreign DNA III which includes a functional, amplifiable gene coding for a different selectable or identifiable trait. Cotransformation is carried out under suitable conditions permitting expression of the trait encoded by DNA III, but not of the trait encoded by DNA II. Cotransformed eucaryotic cells expressing the trait encoded by DNA III are recovered and cloned under appropriate conditions permitting expression of the trait encoded by DNA II. The cloned, cotransformed cells are selected or identified on the basis of expression of the trait encoded by DNA II and recovered. The recovered cells contain multiple copies of DNA I and can be used to produce messenger RNA transcript or proteinaceous product.

Transformation vectors which can be used to introduce foreign DNA into suitable eucaryotic cells are also disclosed.

BRIEF DESCRIPTION OF THE DRAWING

FIG. 1. shows the restriction map of a recombinant plasmid, pdLAT-3, which contains Tk and Aprt gene sequences. More specifically, plasmid pdLAT-3 contains a 2.8 kb Bgl II/Bam HI fragment of the Herpes Simplex Virus genome inserted into the Bam HI site of the vector pBR322. This fragment includes the entire coding sequences of the thymidine kinase gene (■) as well as 1.6 kb of 3' flanking DNA (■), but lacks the promoter and 5' flanking DNA sequences. The initiator AUG is located 50 nucleotides 3' to the Bgl II site. Additional in-phase AUG codons are noted. This plasmid also contains a 4.3 kb Hind III/Bgl II fragment of hamster DNA which contains the entire hamster aprt gene as well as approximately 700 bp of 5' flanking DNA (□). A 2.4 kb Bgl II insert of bacteriophage lambda DNA (λ), originating from positions 36489 to 38935 of the phage genome, separates the hamster and herpes virus DNA sequences. The tk and aprt genes are inserted with opposite polarities.

DETAILED DESCRIPTION OF THE INVENTION

Multiple copies of a foreign DNA I which includes a functional, amplifiable gene coding for production of a proteinaceous product may be introduced into a suitable eucaryotic cell. This result is accomplished by cotransforming the cells with DNA I and with foreign DNA II which includes a functionally deficient, amplifiable gene whose expression is associated with a selectable or identifiable phenotypic trait. The cotransformation of the eucaryotic cells is carried out under suitable conditions permitting production of the proteinaceous product, but not expression of the trait encoded by the gene carried on DNA II. Cotransformed eucaryotic cells producing the desired product are identified and recovered, e.g. by selection, and then cloned under appropriate conditions which permit selection or identification of eucaryotic cells which express the trait encoded by the gene on DNA II. By recovering cotransformed cells which express the functionally deficient gene, one also obtains cells which contain and express multiple copies of DNA I.

Generally, a suitable eucaryotic cell useful in the practice of the invention is a cell which does not produce the proteinaceous product encoded by the amplifiable gene carried on DNA I and which does not express the selectable or identifiable trait encoded by the functionally deficient, amplifiable gene carried on DNA II. However, the invention may be used to obtain enhanced production of a product which is expressed by the cell, but in amounts which are substantially less than the amounts obtained if multiple copies of DNA I are introduced into the cell. Similarly, the invention may be used to obtain enhanced expression of a gene associated with a selectable or identifiable trait where the gene, but not the associated selectable or identifiable trait, is expressed by the cell.

Thus, if protein I is the protein encoded by DNA I and trait II is the trait encoded by DNA II, suitable cells will in general be protein I negative, trait II negative; and cells containing multiple copies of DNA I will be protein I positive, trait II positive.

DNA I and DNA II may be portions or segments of a single molecule or may be separate, physically and chemically unlinked molecules. In this embodiment of the invention, it is presently preferred that they be a single molecule. Moreover, in view of the current understanding of the mechanism of cotransformation, it appears likely that if separate molecules were used, they would be linked during the cotransformation process prior to introduction into the recipient cells' chromosomes.

The gene carried on DNA I may code for production of human or animal growth hormone, insulin, the protein portion of interferon, a clotting factor, an influenza virus antigen, a hepatitis virus antigen, human serum albumen, an antibody or any other protein or proteinaceous material. Of course, if the gene on DNA I codes for such a product, the selection for or identification of transformed cells which contain and express the product may be difficult. By contrast, the process will be more readily accomplished if the DNA I gene codes for a protein associated with a selectable or identifiable trait. Thus, a gene coding for protein product such as adenine phosphoribosyltransferase (aprt), thymidine kinase (tk) from Herpes simplex virus, dihydrofolate reductase (DHFR), xanthine phosphoribosyltransferase (xprt) or aspartate transcarbamoylase (ATCase), each of which is associated with a selectable or identifiable phenotype, may be the gene carried on DNA I. In addition, other genes whose protein products are associated with phenotypes such as drug resistance, e.g., G418 or neomycin resistance, or morphological changes in the receipient cells can be used.

The gene carried on DNA II is a functionally deficient, amplifiable gene. Suitable genes include genes whose primary promoter has been removed and genes containing a structural mutation. Examples are promoterless or otherwise functionally deficient genes coding for the production of thymidine kinase, adenine phosphoribosyltransferase, dihydrofolate reductase, xanthine phosphoribosyltransferase, aspartate transcarbamoylase or for drug resistance, e.g. neomycin or G418 resistance.

Preferably, DNA I and DNA II are carrier-free, cloned genes. If so, certain advantages are obtained such as avoidance of undesired product production and ease of desired product isolation and purification. These advantages are most readily realized if DNA I and DNA II are segments on the same deoxyribonucleic acid molecule.

As used herein, foreign DNA means DNA which is not indigenous to the recipient cell into which it is introduced. Such DNA can be derived from various cells, including different cells of the same cell type as the recipient, e.g. chromosomal DNA from a normal mouse cell line being introduced into a mutant mouse line. It can also be derived from viruses or from bacterial chromosomal, plasmid or bacteriophage DNA. Alternatively, the DNA can be chemically synthesized by base addition or by enzymatic methods such as cDNA synthesis. Different DNAs can be derived from different sources or by different methods. For example, DNA I can be derived from a human cell line and DNA II from a virus.

Suitable conditions for cotransformation are known to those skilled in the art and are described in certain of the publications previously mentioned and in the Experimental Details set forth herein. In the preferred method, DNA I and DNA II are treated with calcium phosphate prior to use in cotransforming the cells. The molar ratio of DNA I to DNA II may vary widely, e.g., from 1000:1 to 1:1. Of course, the ratio will be 1:1 if the DNA I and DNA II are segments of the same DNA molecule. It is also presently preferred that both DNA I and DNA II be carried on DNA molecules which also include bacterial plasmid or phage DNA, more preferably, a single DNA molecule. Finally, in accordance with the present understanding of the mechanism of cotransformation, DNA I and DNA II are likely to be stably integrated into the chromosomal DNA of cotransformed, recipient cells.

Various types of eucaryotic cells may be used in practicing the invention, including cells of animal or plant origin and yeast cells. Mammalian cells are considered particularly suitable for the production of certain products such as human growth hormone or human serum albumen.

Methods of recovering cotransformed cells, of cloning and subcloning such cells and of selecting or identifying cotransformed cells on the basis of phenotypic or genotypic traits, including appropriate conditions, are known to those skilled in the art.

By maintaining eucaryotic cells into which multiple copies of foreign DNA have been introduced according to the method described under suitable conditions, messenger RNA transcripts and protein products can be produced and recovered. Such suitable conditions for transcription and protein production are known to those skilled in the art. The method for introducing multiple copies of a foreign DNA I into a eucaryotic cell involving only DNA I and DNA II can be used to produce certain products. However, if one wishes to introduce into eucaryotic cells multiple copies of foreign DNAs coding for production of numerous, commercially important proteins or proteinaceous products, it is preferred that a foreign DNA III which includes a functional, amplifiable gene coding for a selectable or identifiable trait different from the trait encoded by DNA II also be employed.

Thus, the preferred process for introducing into eucaryotic cells multiple copies of a foreign DNA I which includes a functional, amplifiable gene coding for a desired product comprises cotransforming suitable eucaryotic cells with the DNA I and with a DNA molecule comprising a foreign DNA II which includes a functionally deficient, amplifiable gene coding for a first selectable or identifiable phenotypic trait and a foreign DNA III which includes a functional, amplifiable gene coding for a second, different selectable or identifiable phenotypic trait. The cotransformation is carried out under suitable conditions permitting expression of the gene carried on DNA III and selection or identification of cotransformed cells on the basis of its associated trait but not expression of the gene carried on DNA II or its associated trait. Cotransformed cells expressing the trait associated with the gene on DNA III are recovered and cloned under appropriate conditions permitting selection or identification of eucaryotic cells expressing the gene carried on DNA II. Identification and recovery of such cells also results in identification and recovery of cells containing multiple copies of DNA I. Suitable eucaryotic cells are as described previously. In this embodiment of the invention, doubly mutant cells which do not express either the trait associated with the gene on DNA II or the trait associated with the gene on DNA III may be employed. Preferably, one or both traits are associated with dominant acting genes so that the use of mutant cell lines is not necessary. Thus, for example, use of a gene associated with neomycin resistance confers upon recipient cells a trait not expressed by normal cells so that use of mutant cell lines is not required.

Preferably, DNA I and the molecule carrying DNA II and DNA III are cloned, carrier-free genes and are two separate molecules treated with calcium phosphate prior to cotransformation. The ratio of cloned DNA I to cloned molecule, e.g., plasmid, carrying DNA II and DNA III may vary widely. Preferably, the ratio is in the range from about 650:1 to 25:1.

Foreign DNA I includes a gene coding for production of a protein or protein-containing product. Examples are human and animal growth hormone, insulin, an interferon, a clotting factor, an influenza virus antigen, a hepatitis virus antigen, human serum albumen, an antibody or an enzyme.

The functionally deficient, amplifiable gene on DNA II and the functional, amplifiable gene on DNA III may vary widely. Suitable examples of DNA II have already been mentioned. Suitable examples of DNA III are in general selected from the same group, except that the genes on DNA III are not characterized by a functional deficiency.

In other respects, the method involving use of DNAs I, II and III will be the same as that involving DNAs I and II. Any variations or modifications employed would be apparent to one skilled in the art. As with the process involving use of DNAs I and II, the process involving use of DNAs I, II and III can be employed to produce and recover messenger RNA transcripts of the DNA and of the proteinaceous products encoded thereby.

Figure 1:
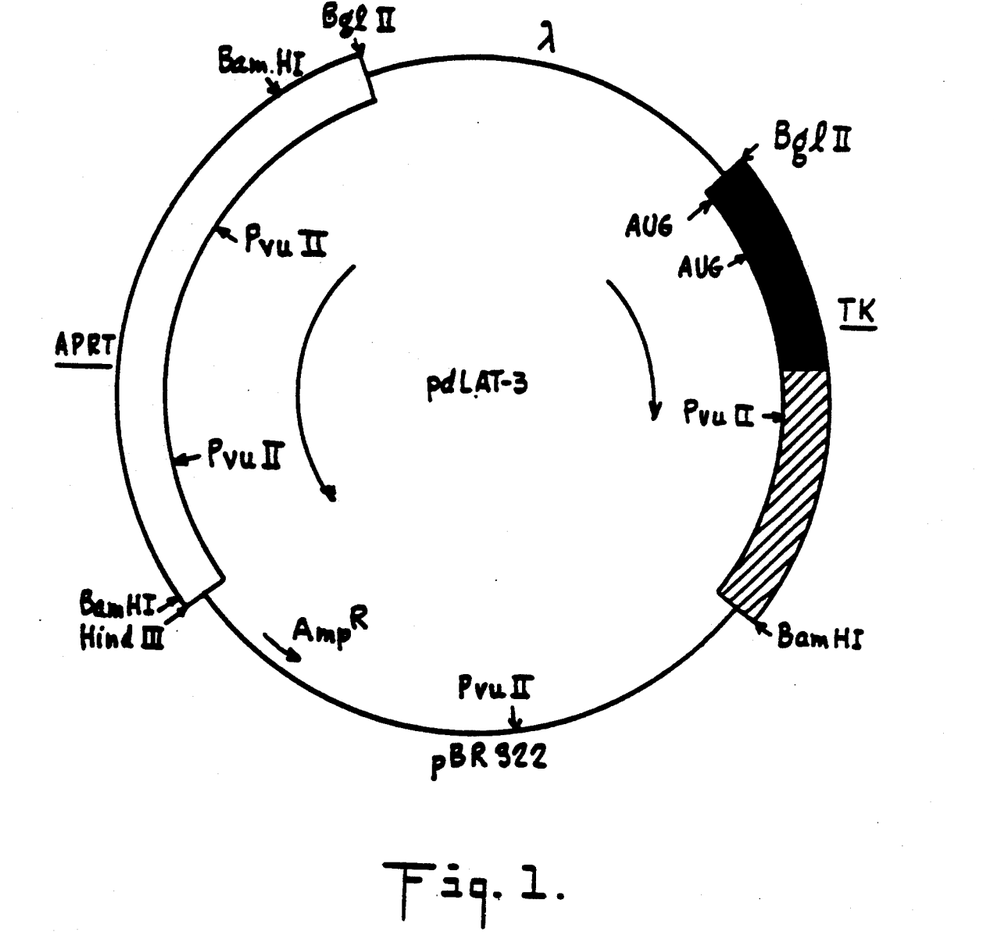

In practicing the invention, deoxyribonucleic acid molecules are used as transformation vectors. Such molecules include those which carry two foreign DNAs, one of which is a foreign DNA II, and additional DNA derived from a noneucaryotic source, e.g., a bacterial plasmid such as pBR322. In the preferred embodiment of the invention, the molecules are circular and include foreign DNA III, foreign DNA II and DNA derived from a noneucaryotic source, e.g., a bacterial plasmid or bacteriophage. An example of such a vector is shown in FIG. 1.

One application of the invention involves its use to introduce into murine Ltk⁻ aprt⁻ cells multiple copies of a cloned, carrier-free gene for human growth hormone. By cotransforming such cells with the cloned human growth hormone gene and with the plasmid pdLAT-3 and then recovering Ltk⁺ aprt⁺ cells according to the method described, cells containing and expressing multiple copies of the human growth hormone gene are obtained and a method for producing human growth hormone is provided.

Another application of the invention involves introducing into eucaryotic cells multiple copies of a plasmid similar to pdLAT-3 except that a functionally deficient, promoterless, amplifiable gene coding for G418 resistance replaces the tk gene.

Still another application of the invention involves introduction of multiple copies of a cloned, carrier-free gene for human growth hormone into eucaryotic cells by cotransforming this gene and a plasmid carrying a functionally deficient, promoterless, amplifiable gene coding for G418 resistance and a functional, amplifiable aprt gene.

EXPERIMENTAL RESULTS

Experimental Design

A system to study gene rearrangements in mammalian cells was developed based upon two predictions: 1) a gene lacking its promoter will not function when introduced into a cell in culture; and 2) rare cell mutants which do express the truncated gene will have undergone some form of genetic rearrangement.

The transcriptional control region for the structural gene encoding the Herpes virus thymidine kinase has been mapped with precision [McKnight, S. L., Gavis, E. R., Kingsbury, R. and Axel, R. (1981). Cell 25, 385-398]. 110 nucleotides of 5' flanking DNA immediately adjacent the site of transcription initiation is essential for expression of the tk gene. Deletions extending into this region result in a striking decrease in specific transcription and a concomitant reduction in transformation efficiency. Initially, a 7.8 kb Hind III fragment containing the hamster aprt gene was inserted into a plasmid containing the intact tk gene. A unique Bgl II site is located within the 5' untranslated region of the tk gene, 50 nucleotides 5' to the initiator ATG. A second Bgl II site in the aprt-tk clone is located within the hamster DNA, 5' to all sequences necessary for aprt expression. The Bgl II fragment delineated by these two sites was excised and replaced with a 2.6 kb fragment of bacteriophage lambda DNA. The consequence of this substitution is the removal of the promoter elements and 5' cap site of the tk gene, while the coding region and poly A addition site remain intact. This plasmid contains a functional aprt gene which is a selectable marker enabling us to introduce the linked, mutant tk gene into mouse Ltk$^-$ aprt$^-$ cells. In this plasmid, the aprt and tk genes have been introduced in opposite polarities, preventing read-through transcription of a tk transcript from an aprt promoter. Transformants constructed with this plasmid display the aprt$^+$ tk$^-$ phenotype. It is anticipated that tk$^+$ variants which emerge from aprt$^+$ tk$^-$ transformants are the result of gross rearrangements rather than local alterations in base sequence.

Mutation to the Aprt$^+$ Tk$^+$ Phenotype

The aprt-tk plasmid was introduced into mouse Ltk$^-$, aprt$^-$ cells as a calcium phosphate precipitate [Wigler, M., Sweet, R., Sim, G. K., Wold, B., Pellicer, A., Lacy, E., Maniatis, T., Silverstein, S. and Axel, R. (1979). Cell 16, 777-785] under conditions which select for the aprt$^+$ phenotype. All aprt$^+$ clones remained tk$^-$. Eight clones were identified which had integrated at least one copy of the aprt-tk plasmid. These characterized clones were independently isolated and tested for the frequency with which they generated tk$^+$ variant subclones. Each of the eight clones was expanded in adenine-azaserine-BUdR, growth conditions which maintain the aprt$^+$ tk$^-$ phenotype of the cell population. Each cell line was then grown for three generations in neutral medium (supplemented only with adenine) and then placed into growth medium that selects for the tk$^+$ phenotype. All eight parental clones produced tk$^+$ progeny at a unique rate ranging from $1.6 \times 10^{-5}$ to $1.8 \times 10^{-7}$ mutants per cell division. All tk$^+$ progeny remained aprt$^+$.

Amplification is Responsible for the Tk$^+$ Phenotype

The structures of the aprt and tk genes in aprt$^+$ tk$^-$ parents as well as 44 tk$^+$ mutant subclones were examined by blot hybridization. Eight tk$^-$ parental clones were shown by blotting to contain one or a few integrated copies of the aprt-tk plasmid. For each clone, digestion of cellular DNA with the enzyme Pvu II produces a diagnostic 5 kb linkage fragment extending from within the aprt gene, through the spacer sequence, and includes the entire tk structural gene (see FIG. 1). A 2.0 kb fragment is also generated which is homologous only to aprt sequences. A third fragment extends from within the aprt gene into flanking DNA. A final additional band is observed which extends from DNA flanking the tk coding sequences into cellular DNA. Hybridization with probes specific for either the tk or aprt genes reveals that in all 44 tk$^+$ clones the copy number of the tk and linked aprt genes has increased 20 to 40 fold. Pvu II-cut DNA was probed with a tk gene sequence and it was found that there is a single copy of the 5.0 kb linkage fragment and thus of the tk gene in the tk$^-$ parent. The intensity of this fragment, as well as the 2.4 kb flanking fragment, increased dramatically in tk$^+$ subclones. The extent of amplification was about 20 to 40 fold. A third fragment, containing an incomplete tk gene, is also contained within the amplification unit. As judged by blot hybridization, concomitant amplification of the linked aprt gene was observed in all tk$^+$ mutants. The unit of DNA which has been amplified not only includes the tk-aprt plasmid, but from 40 to greater than 200 kb of flanking DNA (see below). It should be noted that in 90 percent of the clones tested, the amplification process occurred without gross rearrangement. The linkage between the aprt and tk genes was maintained intact without changes in the flanking fragments.

Amplified Expression of an Aberrant Tk mRNA

In order to determine the mechanism by which amplification renders the cells tk$^+$, an analysis of the RNA transcripts present in the parental tk$^-$ and amplified tk$^+$ cell lines was made. In control populations of cells transformed with a wild-type tk gene, a major 1.3 kb transcript is expressed which is responsible for the synthesis of wild-type tk enzyme. 5' and 3' termini of this message have been mapped with precision, utilizing an S-1 nuclease mapping assay [McKnight, S. L. and Gavis, E. R. (1980). Nucl. Acids Res. 8, 5931-5948]. Some transformants containing a single copy of the wild-type tk gene also express a smaller 0.9 kb transcript. RNA from one such control transformant containing the two transcripts was examined by Northern blot hybridization. Cells containing a single copy of the truncated tk gene plasmid express the 0.9 kb RNA transcript. A second, less abundant 1.1 kb RNA is also expressed. Hybridization with tk probes indicates that both transcripts encode a portion of the tk structural gene. The tk transcripts from one amplified tk$^+$ mutant overproduced the 0.9 kb transcript in proportion with the level of amplification of the truncated tk gene. A second tk$^+$ mutant overproduced the 1.1 kb RNA, initially present at exceedingly low levels in the tk$^-$ parent, to a similar extent.

From these results, it is apparent that a number of alternative transcription start sites exist about the tk gene, some of which are utilized only after the primary promoter has been deleted, suggesting that the aberrantly initiated 0.9 kb message can produce sufficient tk enzyme only when present in the cytoplasm at high copy number. It is likely that this short alternative transcript encodes a similarly shortened tk enzyme, 70 percent the size of the wild-type protein. Examination of the tk gene sequence reveals three in-phase translation initiation codons close to the predicted 5' terminus for this message. This short enzyme is likely to function poorly and only when it is present in abundance is sufficient enzymatic activity accumulated to permit conversion to the tk+ phenotype.

An alternative mechanism by which amplified cell lines display the tk+ phenotype involves the relative overproduction of a 1.1 kb transcript. This RNA is present at very low levels in aprt+ tk− cells, but its synthesis is enhanced upon amplification. These results suggest that this aberrant transcript is regulated by a weak promoter which generates sufficient mRNA only when the tk gene is present in high copy number.

Physical Structure of Amplified DNA

The ability to amplify transforming DNA provides a facile experimental system to study the extent and arrangement of amplified genes. Cotransformation results in the integration of concatenates of transforming DNA, consisting of a single selectable gene along with from 1 to 2,000 kb of carrier DNA at a single locus in the chromosome [Robins, D. M., Ripley, S., Henderson, A. S. and Axel, R. (1981). Cell 23, 29–39; Perucho, M., Hanahan, D. and Wigler, M. (1980). Cell 22, 309–317]. If the carrier DNA consists of a well-defined collection of cloned DNA sequences, the length and order of these sequences in the transforming element can be mapped with precision.

To this end, aprt+ tk− cell lines were constructed with carrier DNA which consisted entirely of 20 plasmid clones containing 5–15 kb inserts of random human DNA sequences inserted into the pBR322 derivative, pAT153. Cell lines constructed in this manner contain a single copy of the tk-aprt plasmid flanked at 5–15 kb intervals by uniquely identifiable pBR sequences. Tk+ mutant subclones were derived from these lines and the organization of amplified DNA was determined by examining the number and arrangement of the amplified pBR sequences.

Genomic DNA was isolated from a tk− parent and eight independently derived tk+ mutant subclones, cleaved, blotted and probed for pBR sequences. The DNA was cut with Bgl II and Xba I, two enzymes which do not cut pBR, so that each integrated pBR will be displayed as a unique band upon blot hybridization. The unamplified tk− parent shows numerous pBR bands of single copy intensity. The eight tk+ subclones have each amplified a subset of the pBR bands.

Four conclusions can be drawn from this experiment. First, the size of the amplification unit is variable, ranging from 40 to greater than 200 kb. By simply counting the number of amplified pBR bands, one obtains a direct estimate of the size of the amplification unit.

Second, despite a common genetic background, each amplification unit is unique. No two tk+ subclones have amplified the same subset of pBR bands.

Third, despite this heterogeneity, a common core of bands is amplified in all clones, and one mutant amplified only this core. The existence of this core suggests that in all clones, amplification initiates at a common point and procedes outward, for varying distances, into flanking DNA. This common point may be the origin of replication for the amplified unit. Since the entire amplified unit consists of pBR clones which have already been identified and recovered, this origin is readily isolatable.

Finally, extensive rearrangement does not occur during amplification. In general, each amplified band is present as a single copy band in the tk− parent. In 10 percent of amplified cell lines, rearrangements about the tk and aprt genes were detected. These rearrangements coexisted with the parental gene organization, suggesting that occasionally gene variants arise during the amplification process. The variant genes are only a fraction of the amplified gene copies.

Genetic Behavior of Amplified DNA

The presence of two selectable markers, aprt and tk, within the amplified unit has made it possible to study the genetic behavior of the amplified DNA. It was asked whether, in a single generation, amplified clones containing multiple aprt genes can mutate to the aprt− tk+ phenotype. These phenotypic requirements are such that the tk gene must remain amplified while all the amplified aprt genes become inactivated.

Initially, aprt− tk+ mutants were isolated in the following manner. A pool of approximately 100 aprt+ tk+ colonies derived from a single unamplified tk− parent were grown in mass culture, placed in neutral medium for three generations and then placed into selection for the aprt− tk+ phenotype. Aprt− tk+ mutants derived from this population were isolated at a frequency of $1.3 \times 10^{-5}$. In addition, 14 independent aprt+ tk+ clones were individually analyzed for mutation rate to the aprt− tk+ phenotype. Twelve of the fourteen lines produced aprt− tk+ mutants at rates ranging from $3 \times 10^{-4}$ to $4 \times 10^{-7}$. Such rates are close to the frequencies with which cells containing a single linked wild-type aprt and wild-type tk gene mutate to the aprt− tk+ phenotype. The isolation of these mutants was therefore quite surprising. If each aprt gene were mutating independently of all other amplified aprt genes, the probability of isolating a cell containing 40 mutant aprt genes would be undetectably small.

A fluctuation analysis [Luria, S. E. and Delbruck, M. (1943). Genetics 28, 491–511] was performed on one amplified cell line to more precisely measure the mutation rate to aprt−. Table 1 summarizes the results of this experiment. The ratio of the variance to the mean is approximately one in the control cultures, the value expected for a Poisson distribution. This rate is much larger in the experimental series, a result which would be expected for the fandom occurrence of mutations during growth in neutral medium prior to the imposition of selective agents. The mutation rate to aprt−, calculated by the fraction of cultures with no mutations [Lea, D. E. and Coulson, C. A. (1949). J. Genet. 49, 264–285] is $1.41 \times 10^{-4}$ mutants per cell division. Finally, this analysis demonstrates that the capacity to mutate to aprt− is a property of every cell, not a unique property of an unusual variant which may have arisen in the derivation of this cell line.

Genotypic Changes in the Mutation to the Aprt− Phenotype

The structure of the tk and aprt genes was examined by blot hybridization in seven aprt− tk+ mutants derived from a population of aprt+ tk+ clones.

TABLE 1

Fluctuation Analysis*

| | Independent Replicas | Mass Culture |
|---|---|---|
| Number of Replicate Cultures | 30 | 1 |
| Number of Samplings per Culture | 2 | 4 |
| Initial Number of Cells per Replicate | 20 | |
| Final Number of Cells per Replicate | $5 \times 10^4$ | $5 \times 10^4$ |
| Number of Duplicates with Zero Aprt$^-$ Tk$^+$ Colonies | 1 | 0 |
| Number of Aprt$^-$ Tk$^+$ Colonies per Replicate | | |
| Range | 0–3,804 | 521–563 |
| Median | 186 | 539 |
| Mean | 436.4 | 545 |
| Variance/Mean | 1,604.3 | 0.49 |
| Mutation Rate | | |
| $F_0$ Calculation | $1.36 \times 10^{-4}$ | |
| Median Calculation | $7.09 \times 10^{-4}$ | |

*For the fluctuation experiment, 30 replicate cultures of an aprt$^-$ tk$^+$ cell line were grown to confluence in neutral medium following seeding with approximately 20 cells per plate. Each plate was then reseeded in duplicate at $5 \times 10^4$ cells per plate and selection was imposed for the aprt$^-$ tk$^+$ phenotype. A mass culture of RA was also maintained in neutral medium and aliquots were similarly placed into selection for the aprt$^-$ tk$^+$ phenotype. Mutation rates were calculated by the methods of Lea, D. E. and Coulson, C. A. (1949) J. Genet. 49, 264-285. The $F_0$ calculation is based upon the fraction of plates with no colonies. The median calculation is based upon the median number of aprt$^-$ tk$^+$ colonies per plate.

*For the fluctuation experiment, 30 replicate cultures of an aprt$^+$ tk$^+$ cell line were grown to confluence in neutral medium following seeding with approximately 20 cells per plate. Each plate was then reseeded in duplicate at $5 \times 10^4$ cells per plate and selection was imposed for the aprt$^-$ tk$^+$ phenotype. A mass culture of RA was also maintained in neutral medium and aliquots were similarly placed into selection for the aprt$^-$ tk$^+$ phenotype. Mutation rates were calculated by the methods of Lea, D. E. and Coulson, C. A. (1949) J. Genet. 49, 264–285. The $F_0$ calculation is based upon the fraction of plates with no colonies. The median calculation is based upon the median number of aprt$^-$ tk$^+$ colonies per plate.

First, the linkage arrangement between the aprt and tk genes was determined by examining the integrity of the 5.0 kb Pvu II fragment which extends from within the aprt gene through the tk gene (see FIG. 1). Secondly, the structure of the aprt gene itself was determined from the integrity of the 4.3 kb Hind III/Bgl II fragment which contains the entire aprt gene.

This analysis revealed two classes of mutants. One class has deleted all the aprt genes. The 4.3 kb Hind III/Bgl II fragment was absent and no information homologous to aprt remained in the genome. The tk genes, as expected, remain amplified. As mentioned above, the aprt$^+$ tk$^+$ amplified clones reveal a diagnostic 5 kb Pvu II fragment reflecting the linkage between aprt and tk present in the donor plasmid. Deletion of a single aprt gene would be expected to produce a single new Pvu II linkage fragment which extends from the tk gene into flanking DNA beyond the extent of the deletion. Multiple independent deletion events required to remove all the aprt genes should therefore generate several new Pvu II fragments. It is striking that in each aprt$^-$ tk$^+$ mutant clone resulting from deletion of all aprt genes, only one amplified Pvu II fragment is observed which differs in size from the original linkage fragment. Independent aprt$^-$ tk$^+$ mutant subclones each show a different single amplified Pvu II fragment. It appears that the deletions were not independent mutation events. A single deletion event has become reiterated in all members of the amplified array.

A second, less frequent class of aprt$^-$ tk$^+$ mutants show no changes in the structure or arrangement of the tk or aprt genes. The 4.3 kb fragment containing the aprt gene along with the diagnostic Pvu II linkage fragment remain unchanged. Furthermore, the extent of amplification of the tk and aprt genes is identical in aprt$^+$ parents and the aprt$^-$ mutants.

A transformation assay was employed to determine whether the aprt$^-$ phenotype in these cell lines results from transmissible alterations in DNA or from phenotypic modulation of aprt expression without concomitant DNA changes. High molecular weight DNA was isolated from an amplified aprt$^+$ cell line and three aprt$^-$ mutants which retain the aprt gene. Aprt$^-$ cells were exposed to each of the four DNA samples and the efficiency with which each sample gave rise to aprt$^+$ colonies was measured. 60 μg of DNA from each of the aprt$^-$ mutant lines produced no colonies. These data indicate that this class of mutants result from heritable changes in DNA not readily detectable by blot analyses.

Aberrant Transcripts Produced by Mutant Aprt Genes

Analysis of the RNA transcripts from these mutant genes reveals alterations in aprt mRNA consistent with the notion that in each aprt$^-$ cell line all amplified aprt genes bear an identical mutation. Cell lines containing a single copy of the wild-type hamster aprt gene express a unique 1 kb transcript in total cellular poly A$^+$ RNA. In aprt$^+$ tk$^+$ cell lines in which the aprt gene has been coamplified with the truncated tk gene, the amount of this mRNA increases in proportion with the extent of amplification. The amplified aprt$^-$ lines, which show no changes in Southern blotting, all show changes in the pattern of RNA transcripts. One cell line was particularly instructive. It does not express the wild-type 1 kb aprt mRNA, but instead produces two aberrant transcripts, both present at amplified levels. It is suggested that these two transcripts result from a mutation which alters the wild-type pattern of splicing. A second mutant line produces two similar aberrant transcripts at strikingly reduced amounts. In a third aprt$^-$ line, a 1 kb mRNA of appropriate size is present at low level, no longer consistent with the extent of amplification. At present, the nature of these mutations or the manner in which they generate the aprt$^-$ phenotype is not understood. Nonetheless, in this class of mutants, as well as with the deletion mutants, it appears that a unique aprt mutation arose in a single aprt gene and through correction processes was transmitted to all the members of the amplified aprt array.

The Physical Structure of Amplified DNA in Aprt$^-$ Mutants

In considering possible mechanisms responsible for the correction process, it is important to discern whether the sequence changes observed are restricted to a localized region about the aprt gene or whether gross reorganization extends throughout the amplified array. The physical changes in the amplification unit upon correction of cell lines constructed solely with defined plasmids were therefore examined. As described above, these cloned cell lines maintain a transforming element which consists of plasmid sequences for which cloned probes are available. In this way, a mapped amplified array can be analyzed before and after correction has occurred. Three aprt$^+$ tk$^-$ lines containing derivatives of the plasmid pBR322 were amplified by selection for the aprt$^+$ tk$^+$ phenotype. A total of 14 amplified subclones were picked and expanded. As expected, in each of these lines, the aprt gene remained linked to the tk gene and significant lengths of the transforming DNA have been amplified 20 to 40 fold. Of these 14 lines, 12 produced aprt$^-$ tk$^+$ mutants at detectable frequencies. It should be emphasized that in each of these lines, the aprt and tk genes amplified faithfully. No evidence was found of the production of variant genes during the amplification process in this set of cell lines.

The structure of the aprt gene was initially examined by blot hybridization in each of these aprt$^-$ tk$^+$ cell lines. In each mutant, aprt information has been deleted. A single deletion has been reiterated in all the units comprising the amplified array. Different deletions occur in different cell lines. Furthermore, in 10 of these mutants one breakpoint of the deletion maps occurs within the aprt gene itself, demonstrating that recombination between repeating pBR sequences is not the mechanism of deletion.

pBR322 sequences were utilized as a probe to examine the organization of the flanking DNA in the amplification unit. Examination indicates that the amplification unit remains essentially unchanged upon correction. Each mutant retains the unique array of plasmid sequences displayed by its aprt$^+$ parent. Two bands amplified in the parent are absent in the aprt$^-$ mutants. Hybridization with aprt gene probe demonstrates that one of these bands contains the aprt gene deleted in the aprt$^-$ mutants. The second band may reflect one breakpoint of the deletion in flanking DNA. Thus, the correction process seems to be highly conservative. Rearrangements are restricted to a unique change about the aprt gene which appears identical in all units of the amplified array.

Chromosomal Arrangement of Amplified DNA

In situ hybridization was used to determine whether the amplified DNA in these cell lines resides within a chromosome or exists as small extrachromosomal elements such as double minute chromosomes [Kaufman, R. J., Brown, P. C. and Schimke, R. T. (1979). Proc. Nat. Acad. Sci. USA 76, 5669-5673].

The location of the amplified DNA in one aprt$^+$ tk$^+$ cell line, RA, and a corrected aprt$^-$ tk$^+$ mutant, RA$^-$, were determined by hybridization in situ. These amplified tk$^+$ cell lines contain about 600 pBR sequences facilitating detection by in situ hybridization. Metaphase spreads were prepared from colcemid-treated cells and hybridized in situ with $^{125}$I-labeled pBR322.

A metaphase plate of the part$^+$ tk$^+$ line RA following hybridization with pBR322 was examined. Labeling was localized to a small metacentric chromosome. Examination of over 25 metaphase plates demonstrated that the amplified DNA appears to occupy a unique chromosomal region. A metaphase plate from an aprt$^-$ derivative of RA was also examined. Following hybridization, labeling was similarly localized to a small metacentric chromosome. Inspection of approximately 50 metaphase plates demonstrated that, following mutation to aprt$^-$, amplified DNA remains within the chromosome.

DISCUSSION

Gene Amplification

An aprt$^-$ tk$^-$ cell has been transformed with a plasmid containing two genes: a wild-type aprt gene linked to a tk gene lacking its promoter. Transformants which integrate a single copy of this plasmid exhibit the aprt$^+$ phenotype but remain tk$^-$. Tk$^+$ variants emerge which result from 20-50 fold amplification of the linked plasmid along with significant lengths of flanking DNA. In some cells, the mutant tk gene produces a short transcript which presumably encodes a truncated protein with reduced enzymatic activity. In other cells, aberrant transcripts result from recognition of apparently weak promoters. In both instances, multiple genes are required to generate sufficient enzyme to convert the cell to the tk$^+$ phenotype.

This experimental design selects for mutations involving gene rearrangements which activate the promoter-less tk gene. Mutations due to rearrangements such as insertion, deletion, or amplification may reflect the capacity of the cell to reorganize its genome in the performance of normal cellular processes. Rearrangement mechanisms responsible for mutation in some genes may be exploited to assure the appropriate function of other genes. Thus, deletions are essential events in the activation of immunoglobulin genes [Sakano, H., K., Heinrich, G. and Tonegawa, S. (1979). Nature 280, 288-294]. More complex transpositions result in the expression of silent sequences determining mating type in yeast [Hicks, J. B. and Herskowitz, J. (1977). Genetics 85, 373-393]. Inversions can both activate and inactivate subsets of surface antigens in procaryotes [Zeig, J., Hilmen, M. and Simon, M. (1978). Cell 15, 237-244]. Finally, amplification of the chorion gene occurs in the course of larval development in Drosophila to increase the production of chorion proteins [Spradling, A. C. (1981). Cell 27, 193-203].

Two general mechanisms have been invoked to explain the events responsible for amplification. Gradual processes, such as unequal crossing-over between sister chromatids has been suggested to explain the slow, stepwise selection required to generate amplified cell lines resistant to specific inhibitors of enzyme activity [Alt, F. W., Kellems, R. E., Bertino, J. R. and Schimke, R. T. (1978). J. Biol. Chem. 253, 1357-1370]. Rapid amplification events may involve localized bursts of replication which escape normal control mechanisms and allow a sequence to be recognized and copied by the replicative machinery more than once per generation. In the present studies, the tk$^+$ phenotype emerges in a single step selection suggesting a rapid mechanism of DNA amplification.

The amplification of a transforming element, consisting solely of a small number of cloned sequences, permits one to characterize the physical structure of the amplified unit. Analysis of the structure of amplified endogenous genes is frequently difficult since amplification may proceed into sequences for which cloned probes are currently unavailable. Examination of the structure of amplified DNA in several independent tk$^+$ cell lines derived from a single parent, and therefore of common genetic background, indicates that each amplification unit is unique. The size of the amplification unit is variable, ranging from 40 to greater than 200 kb. Despite this heterogeneity, a common core of bands is amplified in all clones. Finally, each amplified band is also present in single copy in the parent indicating that extensive rearrangement does not necessarily accompany the amplification process.

The observation that a common set of four core bands is amplified in all tk$^+$ lines derived from a single parent suggests that amplification may proceed from a fixed point or origin. One of these four bands should therefore contain the replicative origin and be readily isolatable. The size of the amplified unit in sibling cell lines, however, is quite variable, implying that the site of termination may not be fixed. Replication and subsequent amplification may proceed varying distances from a unique origin.

Examination of chorion gene amplification [Spradling, A. C. (1981). Cell 27, 193-203] has demonstrated that sequences proximal to a putative chromosomal origin of replication are amplified to a greater extent than those more distal to this locus. The results reported here are consistent with this observation. Furthermore, these results suggest that such an amplification gradient may not be a property of individual cells, but rather is a property of a cell population where component cells have each uniformly amplified a more or less extensive region of chromosomal DNA.

It is likely that any selectable gene mutated in vitro in such a manner as to diminish but not eliminate its activity will amplify upon appropriate selection in vivo. Cotransformation and subsequent amplification of disabled genes, along with other cloned sequences, will permit the production of large quantities of protein products encoded by the cotransformed genes. The ability to select cells which amplify cotransformed DNA also greatly simplifies the task of cloning cotransforming DNA from the recipient cell genome [Perucho, M., Hanahan, D., Lipsich, L. and Wigler, M. (1980). Nature 285, 207-210; Lowy, I., Pellicer, A., Jackson, J., Sim, G. K., Silverstein, S. and Axel, R. (1980). Cell 22, 817-823].

Gene Correction

Aprt$^+$ tk$^+$ lines maintain an amplified array consisting of a mutant tk gene and a wild-type aprt gene. Selection for aprt$^-$ tk$^+$ variants imposes pressure to maintain the amplified tk genes but requires inactivation of over 20 wild-type aprt alleles. Aprt$^-$ tk$^+$ variants arise at inordinately high frequencies. From fluctuation analysis, a mutation rate of $10^{-4}$ can be calculated. Thus, the rate of inactivation of 20 amplified aprt genes approximates that for a single aprt gene. The results of fluctuation tests indicate that this property, the ability to mutate to the aprt$^-$ phenotype, is inherent in all cells in the population and is not restricted to a small subset of variant cells.

Selection for the aprt$^-$ phenotype is imposed in a single generation. However, the multiple genotypic events responsible for the aprt$^-$ phenotype may not occur in one generation but may accumulate in time without phenotypic consequences, until all genes have been inactivated.

Analysis of the structure of the amplified DNA as well as of the aprt mRNA indicates that within a given aprt$^-$ cell, all amplified units bear identical mutations. This suggests a two-step process in which mutation occurs in one aprt gene and is ultimately transmitted to all other aprt genes within the amplified array. This process is termed correction. Although the overall frequency of appearance of aprt$^-$ variants is measurable, one cannot directly measure the rates of its two component steps: mutation and correction. Considering the rate of mutation of a single aprt gene, the present data suggest that correction may be a highly efficient process under the experimental conditions described.

A. Contraction and Re-expansion

Two basic mechanisms have been considered to explain the correction process: contraction:re-expansion and genetic recombination. In its simplest form, contraction:re-expansion would involve mutation of a single aprt gene, deletion of the remaining genes, and subsequent re-amplification to provide a sufficient number of tk genes to maintain the tk$^+$ phenotype. These events would have to occur in one or a few generations to survive the imposed selection condition. This and related explanations are considered highly unlikely. First, the pattern of amplified bands in aprt$^-$ tk$^+$ mutants is virtually identical to the aprt$^+$ tk$^+$ parent. This contrasts with the original amplification process in which all aprt$^+$ tk$^+$ derivatives of a single aprt$^+$ tk$^-$ clone reveal different amplified units. If re-expansion were occurring, one would not expect the new pattern of amplified bands to mimic the profile observed in the parent. Second, the expected frequency of individual steps in this process—mutation, deletion, re-amplification—should approximate $10^{-9}$ or less, a value five orders of magnitude lower than the observed frequency.

One form of the contraction:re-expansion model could involve the existence of amplified units on multiple extrachromosomal elements such as double minutes. Mutation could occur within one element which subsequently accumulates in one cell by random unequal segregation. This explanation is excluded in these studies by the observation that amplified DNA resides on a chromosome in both aprt$^+$ and aprt$^-$ cells.

One form of the contraction:re-expansion model consistent with the present data involves multiple cycles of replication at a single chromosomal locus without subsequent integration of the amplified DNA. This process of "local polytenization" could generate a structure resembling an onion skin [Botchan, M., Topp, W. and Sambrook, J. (1978). Cold Spring Harbor Symp. Quant. Biol. 43, 709-719]. This process has been suggested to explain the amplification of integrated viral genes [Botchan, M., Topp, W. and Sambrook, J. (1978). Cold Spring Harbor Symp. Quant. Biol. 43, 709-719] as the specific developmental amplification of Drosophila chorion genes [Spradling, A. C. (1981). Cell 27, 193-203]. Adapting this model to these studies, amplification in the aprt$^+$ tk$^-$ parent would require the presence of a mutant origin of replication in the vicinity of the integrated aprt-tk plasmid. The properties of this mutant origin would permit a localized region of DNA to escape normal growth controls and undergo multiple rounds of replication within a single cell cycle. In the next generation, all unintegrated amplified DNA must be discarded and the mutant origin then regenerates the "onion-skin" during each successive cycle. It should be noted that the involvement of mutant origins requires that the amplified DNA be discarded at each generation to prevent the exponential accumulation of amplified sequences with each successive cell cycle. In such a model, mutation from aprt$^+$ tk$^+$ to aprt$^-$ tk$^+$ need only require mutation within the single integrated aprt gene. The wild-type unintegrated aprt DNA is discarded at the next generation and the mutated, integrated DNA replicates to an amplified state. This interesting possibility is consistent with the present data and is open to experimental test.

B. Genetic Recombination

One final mechanism for correction which must be considered involves genetic recombination. In eucaryotes, individual repeat units in a tandem array frequently show striking homogeneity. Maintenance of sequence homogeneity is thought to arise either by unequal crossing-over events or gene conversion [Smith, G. P. (1976). Science 191, 528-535; Szostak, J. W. and Wu, R. (1980). Nature 284, 426-430; Klein, H. L. and Petes, J. D. (1981). Nature 289, 144-148]. Direct estimates of the frequency of unequal sister strand exchange among repeated DNA sequences in mitotic yeast cells suggest this mechanism can maintain the observed homogeneity [Szostak, J. W. and Wu, R. (1980). Nature 284, 426-430]. Unequal crossing-over is considered an unlikely explanation for the fixation of the mutant aprt gene for two reasons. First, unequal crossing-over between the highly repeated pBR sequences in these cell lines would scramble their relationship to one another, resulting in an altered Southern blot banding pattern, which is not the case. Second, only 30 generations elapse between the creation of these cell lines and the imposition of selection for the aprt$^-$ phenotype. Computer simulations of the unequal crossing-over process has indicated that the probability of fixation of a mutant allele in an array of 30 wild-type genes in such a few generations less than $10^{-8}$, assuming one sister chromatid exchange per generation.

Gene conversion may occur upon strand exchange between sequences of incomplete homology. Regions of non-homology are then corrected, frequently in a non-reciprocal fashion. Recent analysis of the genetic behavior of gene duplications in yeast suggest conversion is the most frequent mechanism of recombination between duplicated elements [Klein, H. L. and Petes, J. D. (1981). Nature 289, 144-148; Jackson, J. A. and Fink, G. E. (1981). Nature 292, 306-311]. Correction to the aprt$^-$ state may therefore result from repeated strand pairing between a mutant and wild-type aprt gene and subsequent conversion of all wild-type genes to the mutant genotype. This mechanism must operate with high frequency to account for the correction observed.

Gene conversion has been implicated in the developmental process of mating type interconversion in yeast [Haber, J. E., Rogers, D. T. and McCusker, J. H. (1980). Cell 22, 277-289; Klar, A. J., McIndoo, J., Strathern, J. W. and Hicks, J. B. (1980). Cell 22, 291-298] and in the maintenance of sequence identity among repeated genes [Sleightom, J. L., Blechl, A. E. and Smithies, O. (1980). Cell 21, 627-638; Scherer, S., and Davis, R. W. (1980). Science 209, 1380-1384; Jackson, J. A. and Fink, G. R. (1981). Nature 292, 306-311]. This mechanism may thus be important in maintaining other essential processes in somatic cells but is evident only when appropriate selection is imposed. Whatever the mechanism for correction of amplified aprt genes in these studies, it is apparent that the transformants analyzed possess a sophisticated mechanism designed to maintain sequence homogeneity among repeated genetic elements.

EXPERIMENTAL PROCEDURES

Cell Culture

Murine Ltk$^-$ aprt$^-$ cells were maintained in Dulbecco's modified Eagle's medium (DME) supplemented with 10 percent calf serum (M. A. Bioproducts) and 50 µg/ml diaminopurine (DAP). Aprt$^+$ tk$^-$ transformants were selected in DME, 10 percent calf serum, 4 µg/ml azaserine, 15 µg/ml adenine (DME+AzAd) [Wigler, M., Sweet, R., Sim, G. K., Wold, B., Pellicer, A., Lacy, E., Maniatis, T., Silverstein, S. and Axel, R. (1979). Cell 16, 777-785]. Aprt$^+$ tk$^-$ transformants were maintained in DME+AzAd plus 30 µg/ml BUdR. Aprt$^+$ tk$^+$ mutants were selected in DME, 10 percent calf serum, 15 µg/ml hypoxanthine, 1 µg/ml aminopterin, 5 µg/ml thymidine (DME+HAT) [Wigler, M., Silverstein, S., Lee, S. L., Pellicer, A., Cheng, Y. and Axel, R. (1977). Cell 11, 223-232]. Aprt$^+$ tk$^+$ cell lines were subsequently maintained in DME, 10 percent calf serum, 15 µg/ml adenine, 1 µg/ml aminopterin, and 5 µg/ml thymidine (DME+AAT). Aprt$^-$ tk$^+$ mutants were selected and maintained in DME+HAT and 100 µg/ml diaminopurine (DME+HAT+DAP).

Transformation of Ltk$^-$ aprt$^-$ Cells

Ltk$^-$ aprt$^-$ cells were transformed with 20 ng of the aprt-tk construct, plasmid pdLAT-3, (linearized with Sal I) as described previously [Graham, F. L. and van der Eb, A. J. (1973). Virology 52, 456-467; Wigler, M., Silverstein, S., Lee, S. L., Pellicer, A., Cheng, Y. and Axel, R. (1977). Cell 11, 223-232]. Some cell lines were cotransformed with 1 µg of carrier DNA consisting entirely of 20 different random clones of human DNA constructed by inserting human DNA into the pBR322 derivative, pAT-153.

Selection for Tk$^+$ Aprt$^+$ Mutant Subclones

Aprt$^+$ tk$^-$ transformants were expanded in DME+AzAd+BUdR. Cells were then grown in neutral medium for three generations (DME+Adenine) and then split out to $5 \times 10^5$ cells per plate in DME+AAT. Mutation rates were calculated using the formula rate:

$$2\ln2\left(\frac{M}{N}\right)/G$$

where M=number of mutant colonies isolated; N=number of cells placed into selection and G=number of generations growth in neutral medium.

Selection for Aprt$^-$ Tk$^+$ Mutants

Aprt$^+$ tk$^-$ clones were amplified by selection for the aprt$^+$ tk$^+$ phenotype. Such clones were picked and expanded for approximately 20 generations on selective medium (DME+AAT). Cells were then replated at $5 \times 10^5$ cells per plate, grown in neutral medium for three days (DME+hypoxanthine+adenine+thymidine) and then placed into selection for the aprt$^-$ tk$^+$ phenotype (DME+HAT+DAP). Mutation rates were calculated as described above.

Blot Hybridization

Cell DNAs were digested with 2 u nuclease/µg DNA for 2 hours. Samples were electrophoresed on 0.8 percent agarose slab gels (10 µg DNA per slot) in 40 mM Tris, 4 mM NaAcetate, 1 mM EDTA, pH 7.9. DNA fragments were transferred to nitrocellulose paper [Southern, E. M. (1973). J. Mol. Biol. 98, 503-517], and the filters were hybridized, washed, and exposed to X-ray film as previously described [Weinstock, R., Sweet, R., Weiss, M., Cedar, H. and Axel R. (1979). Proc. Nat. Acad. Sci. USA 75, 1299-1303; Wigler, M., Sweet, R., Sim, G. K., Wold, B., Pellicer, A., Lacy, E., Maniatis, T., Silverstein, S. and Axel, R. (1979). Cell 16, 777-785]. DNA probes for the tk gene [Pellicer, A., Robins, D., Wold, B., Sweet, R., Jackson, J., Lowy, I., Roberts, J. M., Sim, G. K., Silverstein, S. and Axel, R. (1980). Science 209, 1414-1422] include either the 3.6 kb Bam HI fragment or the 1.9 kb Hinf fragment, and for the aprt gene [Lowy, I., Pellicer, A., Jackson, J., Sim, G. K., Silverstein, S. and Axel, R. (1980). Cell 22, 817–823] the 2.0 kb Hinc II fragment. Probes were nick-translated to a specific activity of 0.5–1×10$^9$ cpm/μg with α-$^{32}$P deoxynucleotide triphosphates [Weinstock, R., Sweet, R., Weiss, M., Cedar, H. and Axel, R. (1979). Proc. Nat. Acad. Sci. USA 75, 1299–1303].

Total cellular RNA was prepared in a procedure employing guanidine thiocyanate and hot phenol extractions. 0.5–1.0 ml of 4M guanidine-thiocyanate was added per 60 ml tissue culture dish. The cells are dripped into a dounce, heated to 60° C. They are then dounced until homogeneous. 10 ml of hot phenol was added to the lysate and mixed at 60° for 5 minutes. 10 ml of chloroform was added and 10 ml of NaAcetate 0.1M, pH 5. It was shaken at 60° for 10 to 15 minutes, chilled on ice for 5 minutes and spun. The aqueous phase is removed and the extraction was repeated with phenol and chloroform. It was then shaken at 60°, chilled, spun and the extraction repeated one more time. The supernatant was ethanol precipitated.

Poly A selection was carried out as described in Aviv, H. and Leder, P. (1972) Proc. Nat. Acad. Sci. USA 69, 1408–1412. RNA blotting onto nitrocellulose was carried out using agarose-formaldehyde gels [Lehrach, H., Diamond, D., Wozney, J. M. and Boedtker, H. (1977). Biochemistry 16, 4743–4751] under the conditions described in Goldberg, D. (1980) Proc. Nat. Acad. Sci. USA 77, 5794–5798.

Computer Simulations

A computer program was designed to determine the probability with which a single mutant allele in an array of n wild-type alleles could comprise the entire array in m generations through sister chromatid exchange. Variables include initial number of gene copies in the repeating array, initial position in the array of the mutant allele, minimum permissible size for the array as a consequence of an unequal crossover event, and maximum extent of misregister during sister chromatid pairing.

What is claimed is:

1. A process for generating in eucaryotic cells multiple copies of foreign DNA I which comprises:
   a) cotransforming suitable eucaryotic cells with said foreign DNA I and with foreign DNA II, said foreign DNA II including a functionally deficient thymidine kinase or adenine phosphoribosyltransferase gene whose primary promoter has been removed, said foreign DNA I including a functional gene coding for production of a desired proteinaceous product, said functional and functionally deficient genes being different;
   b) said cotransformation being carried out under conditions permitting production of the desired product encoded by the gene on DNA I but not expression of the selectable or identifiable trait encoded by the gene on DNA II;
   c) recovering the resulting cotransformed eucaryotic cells producing the desired proteinaceous product;
   d) cloning the cotransformed cells so recovered under conditions permitting selection or identification of calls which express the selectable or identifiable trait encoded by the gene on DNA II;
   e) recovering the then resulting cloned cells and thereby obtaining eucaryotic cells which contain multiple copies of DNA I.

2. A process according to claim 1, wherein the eucaryotic cells do not express the selectable or identifiable trait encoded by the functionally deficient, gene carried on DNA II.

3. A process according to claim 1, wherein the eucaryotic cells do not produce the desired proteinaceous product encoded by the functional, gene carried on DNA I.

4. A process according to claim 1, wherein the eucaryotic cells do not express the selectable or identifiable trait encoded by the functionally deficient, amplifiable gene carried on DNA I and do not produce the desired proteinaceous product encoded by the functional, gene carried on DNA II.

5. A process according to claim 1, wherein the DNA I and DNA II are both carried on a single deoxyribonucleic acid molecule.

6. A process according to claim 1, wherein the foreign DNA I and DNA II are carried on separate, unlinked deoxyribonucleic acid molecules.

7. A process according to claim 1, wherein the gene of DNA I is from Herpes simplex virus and codes for production of thymidine kinase.

8. A process according to claim 1, wherein the gene of DNA I codes for production of dihydrofolate reductase.

9. A process according to claim 1, wherein the gene of DNA I codes for production of human or animal growth hormone, insulin, an interferon, a clotting factor, an influenza virus antigen, a hepatitis virus antigen, human serum albumen or an antibody and the eucaryotic cells are cells capable of selection or identification on the basis of such production.

10. A process according to claim 1, wherein the gene carried on DNA II is a gene containing a structural mutation.

11. A process according to claim 1, wherein the gene carried on DNA II is derived from a gene coding for production of thymidine kinase or adenine phosphoribosyltransferase.

12. A process according to claim 1, wherein the functionally deficient gene carried on DNA II is a thymidine kinase gene.

13. A process according to claim 1, wherein DNA I and DNA II are carrier-free, cloned genes.

14. A process according to claim 5, wherein DNA I and DNA II are carrier-free, cloned genes.

15. A process according to claim 1, wherein DNA I is attached to bacterial plasmid or phage DNA.

16. A process according to claim 1, wherein DNA II is attached to bacterial plasmid or phage DNA.

17. A process according to claim 1, wherein DNA I is treated with calcium phosphate prior to cotransforming the eucaryotic cells.

18. A process according to claim 1, wherein DNA II is treated with calcium phosphate prior to cotransforming the eucaryotic cells.

19. A process according to claim 1, wherein the eucaryotic cells are mammalian cells.

20. A process according to claim 1, wherein DNA I is incorporated into the chromosomal DNA of the cotransformed cells.

21. A process according to claim 1, wherein DNA II is incorporated into the chromosomal DNA of the cotransformed cells.

22. Eucaryotic cells into which foreign DNA I has been introduced by the process of claim 1.

23. Mammalian cells into which foreign DNA I has been introduced by the process of claim 19.

24. A process for producing messenger RNA transcripts complementary to a foreign DNA I which comprises introducing into eucaryotic cells multiple copies of a foreign DNA I using the process of claim 1 and maintaining the cells under suitable conditions for transcription of DNA I into messenger RNA.

25. A process for obtaining messenger RNA transcripts which comprises producing the transcripts using the process of claim 24 and recovering the transcripts so produced.

26. A process for producing a proteinaceous product which comprises producing in eucaryotic cells messenger RNA transcripts complementary to a foreign DNA I using the process of claim 24 and maintaining the cells under appropriate conditions for translation of the transcripts into proteinaceous product.

27. A process for obtaining a proteinaceous product which comprises producing proteinaceous product using the process of claim 26 and recovering the product so produced.

28. A process for generating in eucaryotic cells multiple copies of foreign DNA I which comprises:
   a) cotransforming suitable eucaryotic cells with said foreign DNA I and with a DNA molecule which includes a foreign DNA II and a foreign DNA III, said foreign DNA II including a functionally deficient thymidine kinase or adenine phosphoribosyltransferase gene whose primary promoter has been removed, said foreign DNA III including an amplifiable gene coding for a dominant, second selectable or identifiable phenotypic trait, said foreign DNA I including a functional gene coding for production of a desired proteinaceous product, said functional and functionally deficient genes being different;
   b) said cotransformation being carried out under conditions permitting selection or identification of cotransformed cells expressing said dominant, second phenotypic trait but not the first selectable or identifiable trait encoded by the gene on DNA II;
   c) recovering the resulting cotransformed cells expressing said dominant, second phenotypic trait;
   d) cloning the cotransformed cells so recovered under conditions permitting selection or identification of cells which express the first selectable or identifiable trait encoded by the gene on DNA II;
   e) recovering the then resulting cloned cells and thereby obtaining eucaryotic cells which contain multiple copies of DNA I.

29. A process according to claim 28, wherein the eucaryotic cells do not express the first selectable or identifiable trait encoded by the functionally deficient, gene carried on DNA II.

30. A process according to claim 28, wherein the eucaryotic cells do not express the second selectable or identifiable trait encoded by the functional, gene carried on DNA III.

31. A process according to claim 28, wherein the eucaryotic cells do not express the first or the second trait.

32. A process according to claim 28, wherein DNA I, DNA II and DNA III are carried on the same deoxyribonucleic acid molecule.

33. A process according to claim 28, wherein DNA I is carried on a separate unlinked deoxyribonucleic acid molecule from that which carries DNA II and DNA III.

34. A process according to claim 28, wherein the gene of DNA I codes for production of human or animal growth hormone, insulin, interferon, a clotting factor, an influenza virus antigen, a hepatitis virus antigen, human serum albumen or an antibody.

35. A process according to claim 28, wherein the functionally deficient, gene carried on DNA II is a thymidine kinase gene from Herpes simplex virus whose primary promoter has been removed.

36. A process according to claim 28, wherein the gene carried on DNA III is a gene coding for production of dihydrofolate reductase or for neomycin resistance.

37. A process according to claim 28, wherein DNA I, DNA II and DNA III are carrier-free, cloned genes.

38. A process according to claim 37, wherein DNA I, DNA II and DNA III are carrier-free, cloned genes.

39. A process according to claim 28, wherein DNA II, DNA III and a bacterial plasmid or phage DNA are carried on the same DNA molecule.

40. A process according to claim 28, wherein said foreign DNA I is treated with calcium phosphate prior to cotransforming the cells.

41. A process according to claim 28, wherein DNA II and DNA III are treated with calcium phosphate prior to cotransferring the cells.

42. A process according to claim 28, wherein eucaryotic cells are mammalian cells.

43. A process according to claim 28, wherein DNA I is incorporated into the chromosomal DNA of the cotransformed cells.

44. A process according to claim 28, wherein DNA II and DNA III are incorporated into the chromosomal DNA of the cells.

45. Eucaryotic cells into which DNA I has been introduced by use of the process of claim 28.

46. Mammalian cells into which DNA I has been introduced by use of the process of claim 42.

47. A process for producing messenger RNA transcripts complementary to a foreign DNA I which comprises introducing into eucaryotic cells multiple copies of a foreign DNA I using the process of claim 28 and maintaining the cells under suitable conditions for transcription of DNA I into messenger RNA.

48. A process for obtaining messenger RNA transcripts which comprises producing the transcripts using the process of claim 47 and recovering the transcripts so produced.

49. A process for producing a proteinaceous product which comprises producing in eucaryotic cells messenger RNA transcripts complementary to a foreign DNA I using the process of claim 47 and maintaining cells under appropriate conditions for translation of the transcripts into the proteinaceous product.

50. A process for obtaining a proteinaceous product which comprises producing the proteinaceous product using the process of claim 49 and recovering the product so produced.

* * * * *